US012605219B2

(12) United States Patent
Kaneko

(10) Patent No.: US 12,605,219 B2
(45) Date of Patent: Apr. 21, 2026

(54) RADIO FREQUENCY SURGICAL INSTRUMENT

(71) Applicant: KANEKA CORPORATION, Osaka (JP)

(72) Inventor: Takuya Kaneko, Okaya (JP)

(73) Assignee: KANEKA CORPORATION, Osaka (JP)

( * ) Notice: Subject to any disclaimer, the term of this patent is extended or adjusted under 35 U.S.C. 154(b) by 820 days.

(21) Appl. No.: 17/800,832

(22) PCT Filed: Jan. 19, 2021

(86) PCT No.: PCT/JP2021/001554
§ 371 (c)(1),
(2) Date: Aug. 18, 2022

(87) PCT Pub. No.: WO2021/176862
PCT Pub. Date: Sep. 10, 2021

(65) Prior Publication Data
US 2023/0082615 A1 Mar. 16, 2023

(30) Foreign Application Priority Data

Mar. 5, 2020 (JP) .................................. 2020-038076

(51) Int. Cl.
*A61B 34/30* (2016.01)
(52) U.S. Cl.
CPC .................................... *A61B 34/30* (2016.02)
(58) Field of Classification Search
CPC ...... A61B 18/1492; A61B 2018/00166; A61B 2018/144; A61B 2018/1475; A61N 1/059
See application file for complete search history.

(56) References Cited

U.S. PATENT DOCUMENTS 5,323,768 A 6/1994 Saito et al.
10,045,818 B2 * 8/2018 Kobayashi ......... A61B 18/1492
(Continued)

FOREIGN PATENT DOCUMENTS

JP H057597 A * 7/1991
JP H05115492 A * 4/1992
(Continued)

OTHER PUBLICATIONS

International Search Report for PCT/JP2021/001554 mailed on Apr. 6, 2021.
(Continued)

*Primary Examiner* — Linda C Dvorak
*Assistant Examiner* — William Mossbrook
(74) *Attorney, Agent, or Firm* — Birch, Stewart, Kolasch & Birch, LLP

(57) ABSTRACT

A radio frequency surgical instrument includes a tubular body; a metal wire having a tip end and a base end, and including a first portion exposed from and disposed outside a distal portion of the tubular body and a second portion disposed in the first lumen; and a fixture fixed to a tip end portion of the wire, being in contact with an inner wall of the first lumen, and having a tip end and a base end, wherein the fixture has a first segment including a portion decreased in outer diameter toward the tip end, and when the first segment is equally tripartitioned into a tip portion, a center portion, and a base portion, a base end of the tip portion in the first segment and a base end of the base portion in the first segment are different in radial sectional shape of the fixture.

19 Claims, 8 Drawing Sheets

(56) References Cited

U.S. PATENT DOCUMENTS

| | | | | | |
|---|---|---|---|---|---|
| 2004/0172018 | A1* | 9/2004 | Okada | ................ | A61B 18/1402 |
| | | | | | 606/46 |
| 2006/0247494 | A1* | 11/2006 | Nakagawa | ............. | A61B 1/018 |
| | | | | | 600/104 |

FOREIGN PATENT DOCUMENTS

| | | |
|---|---|---|
| JP | 5-7597 | 1/1993 |
| JP | 5-115492 A | 5/1993 |
| JP | 2000-262537 A | 9/2000 |

OTHER PUBLICATIONS

Written Opinion of the International Searching Authority for PCT/
JP2021/001554 mailed on Apr. 6, 2021.

* cited by examiner

[FIG. 1]
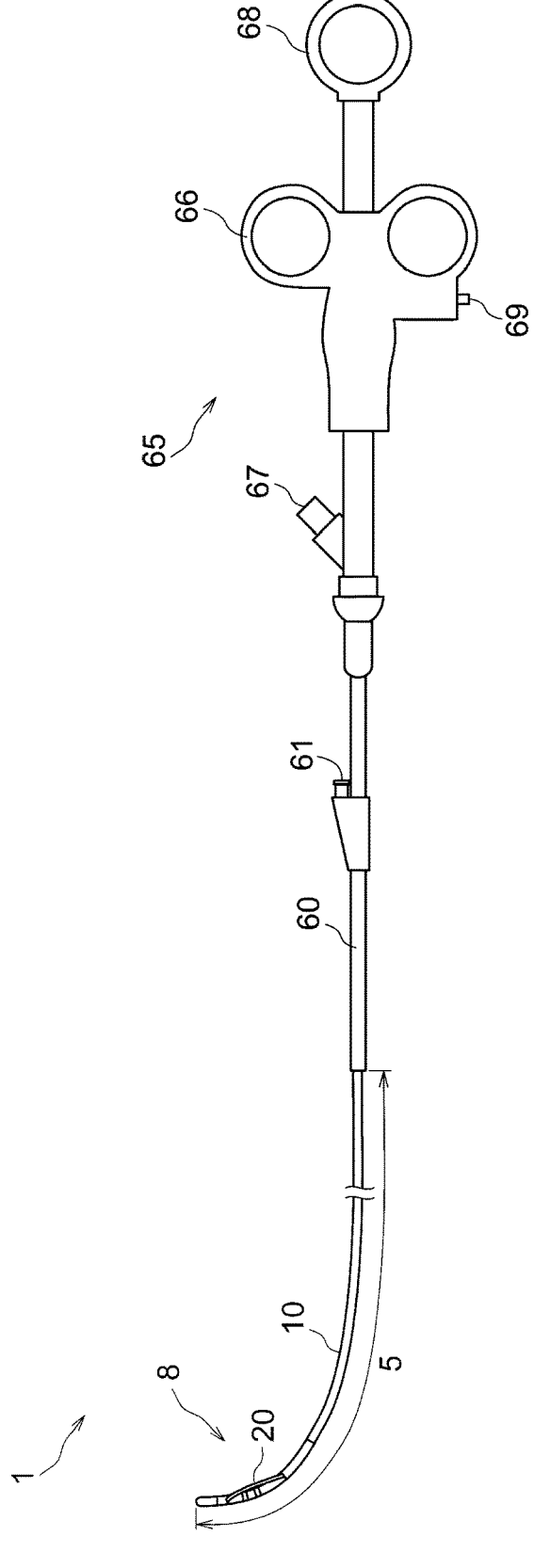

[FIG. 2]
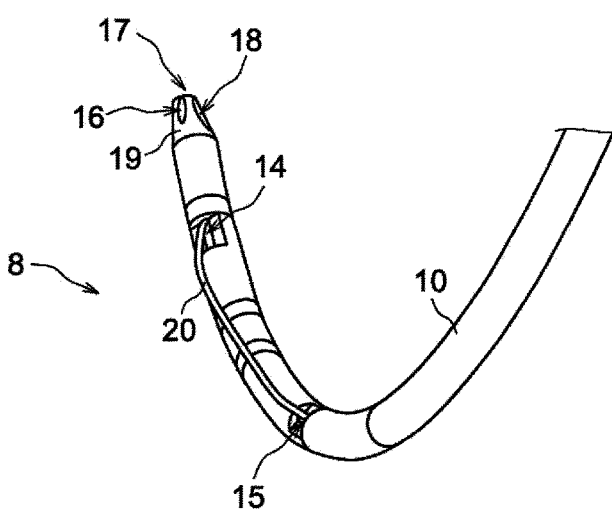
[FIG. 3]
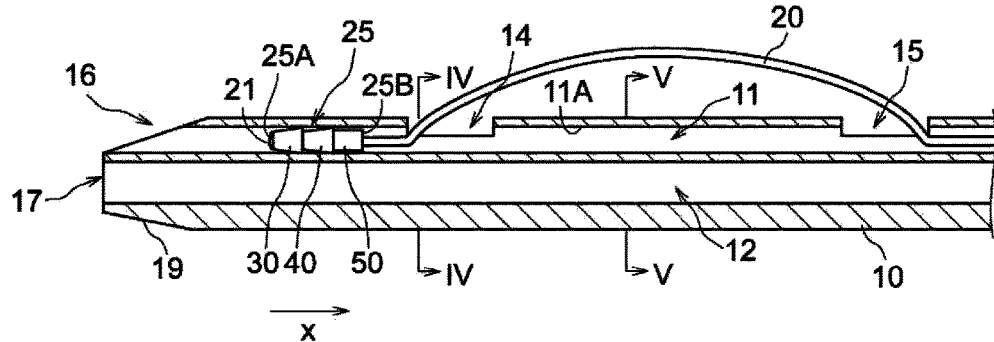
[FIG. 4]
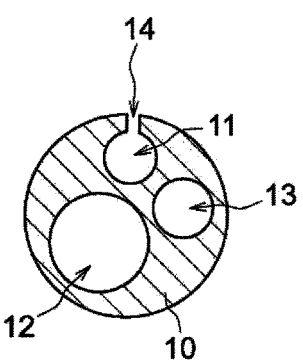
[FIG. 5]
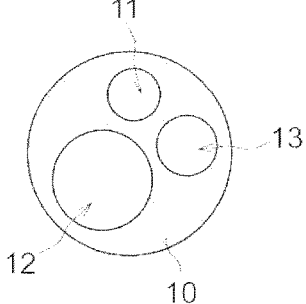

[FIG. 6]
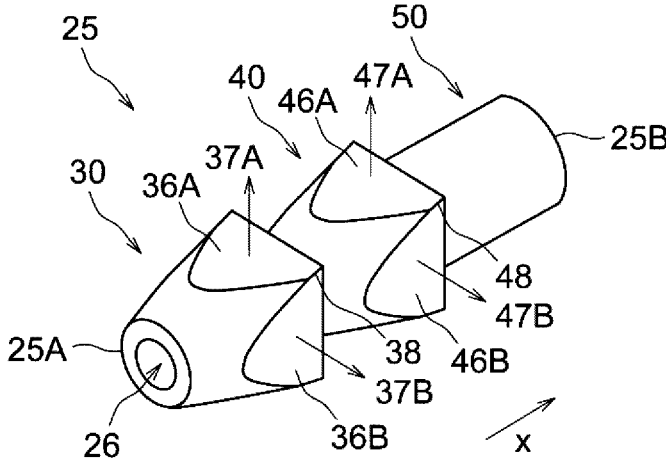
[FIG. 7]
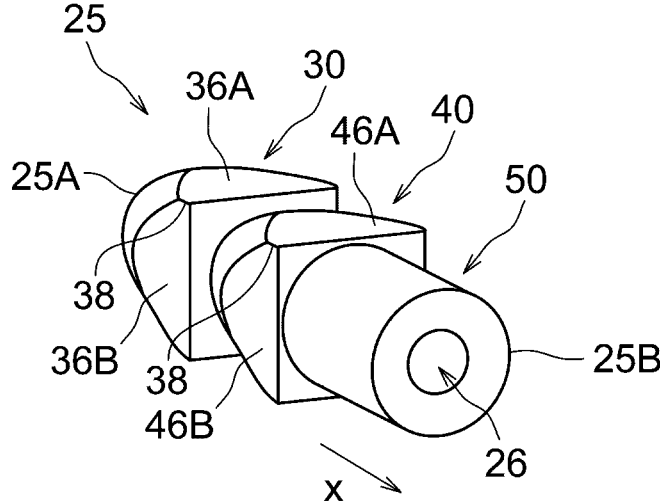
[FIG. 8]
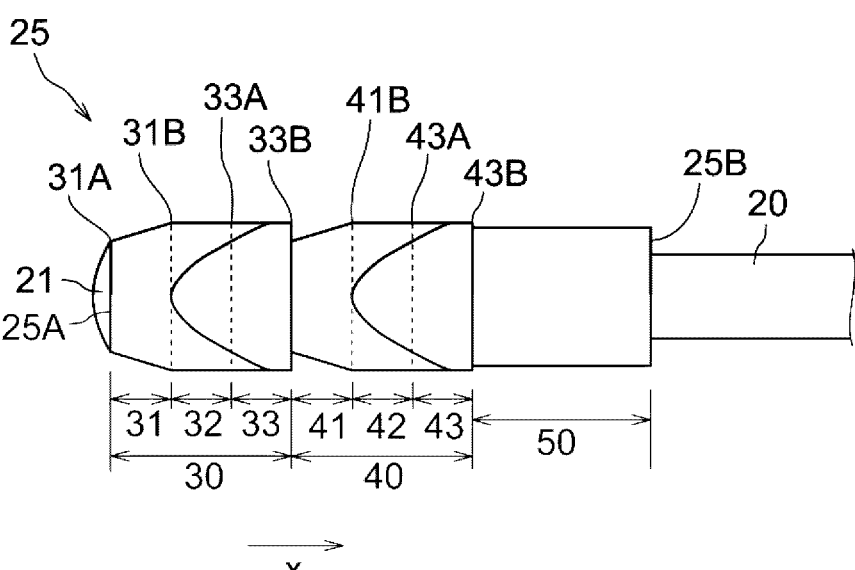

[FIG. 9]
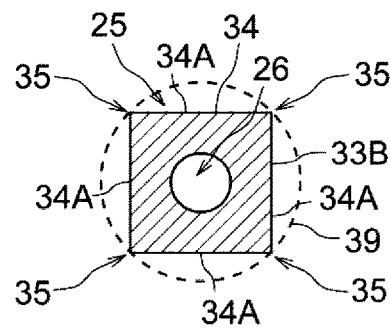
[FIG. 10]
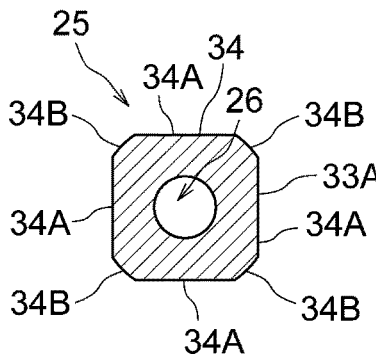
[FIG. 11]
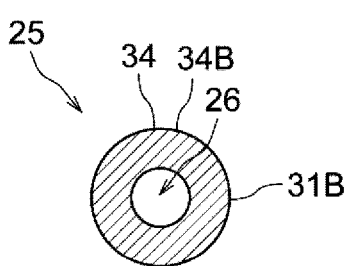
[FIG. 12]
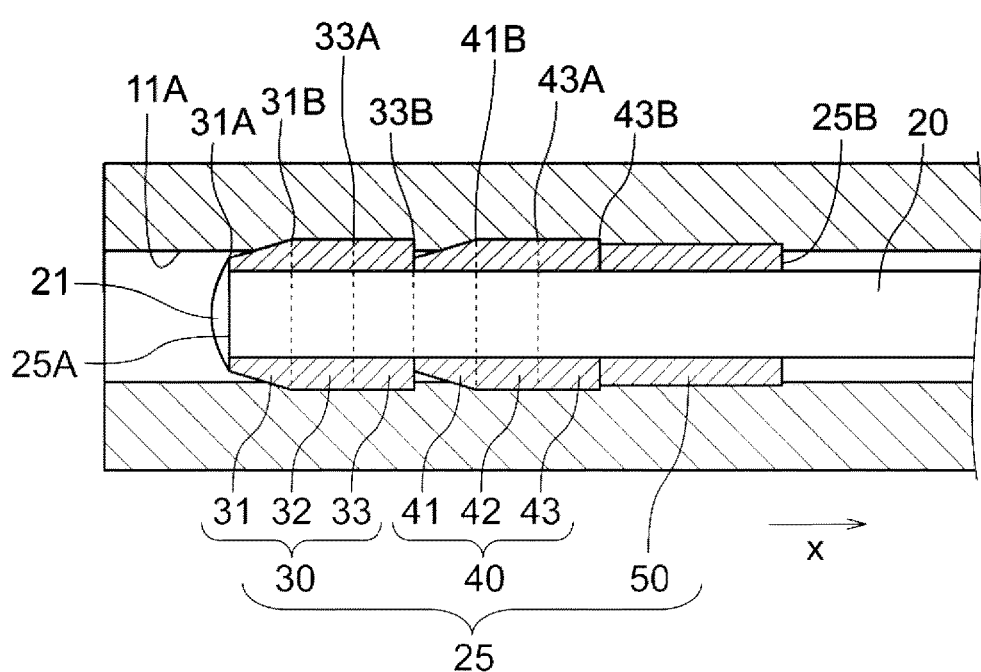

[FIG. 13]
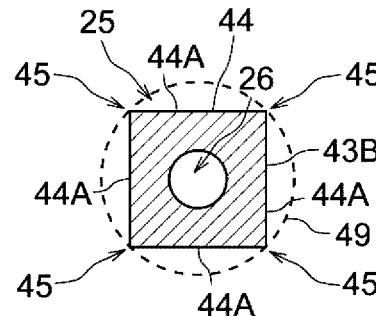
[FIG. 14]
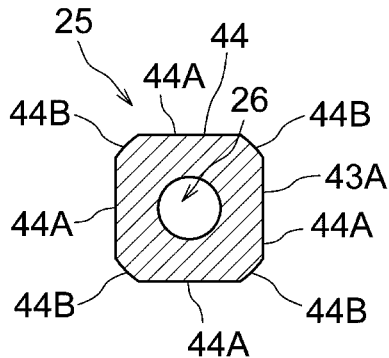
[FIG. 15]
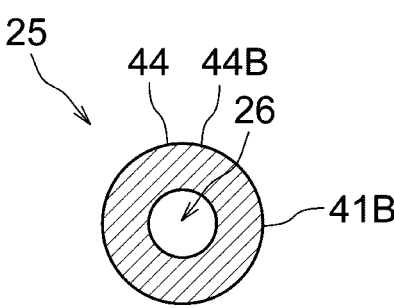
[FIG. 16]
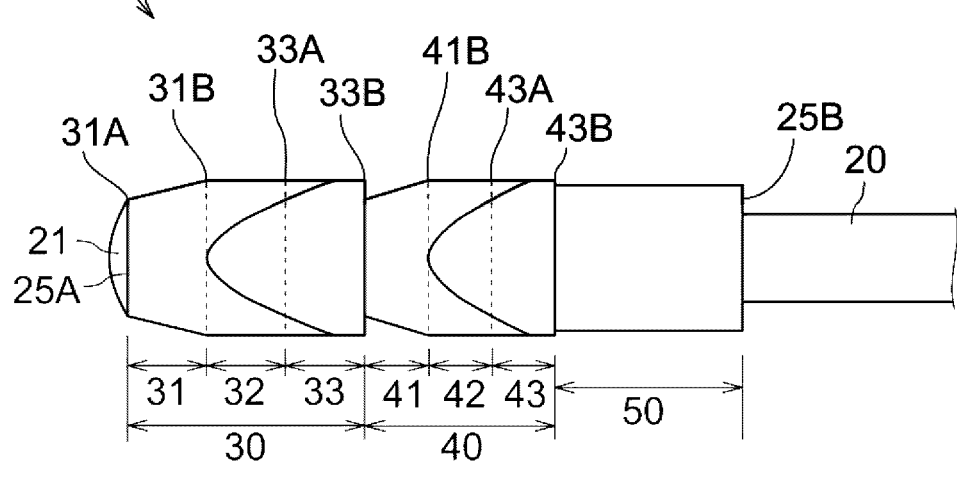

[FIG. 17]
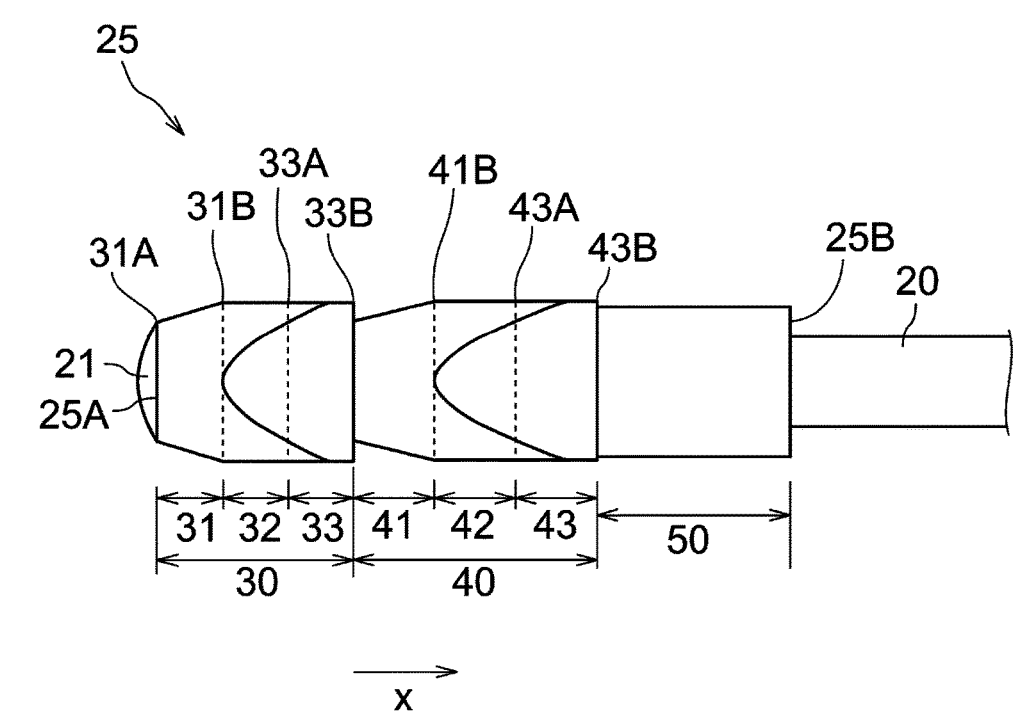
[FIG. 18]
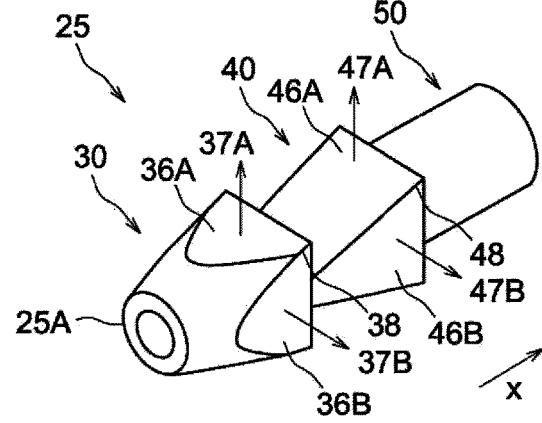

[FIG. 19]
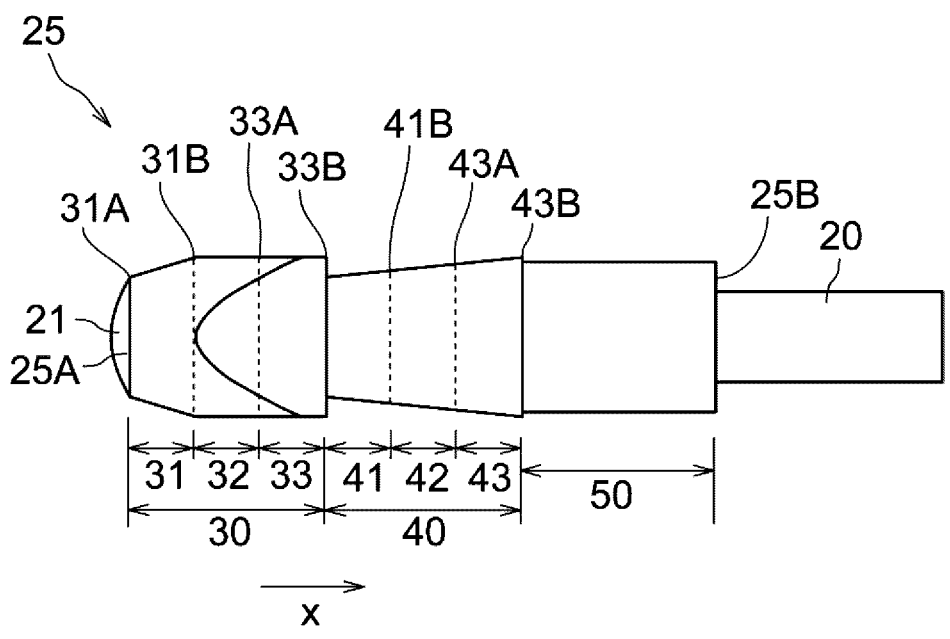
[FIG. 20]
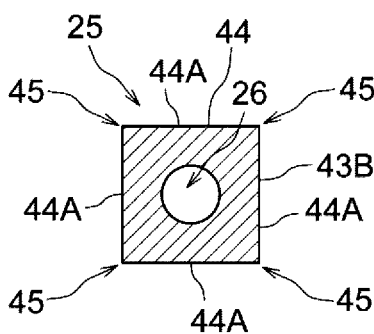
[FIG. 21]
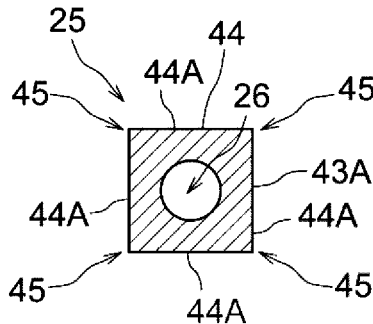
[FIG. 22]
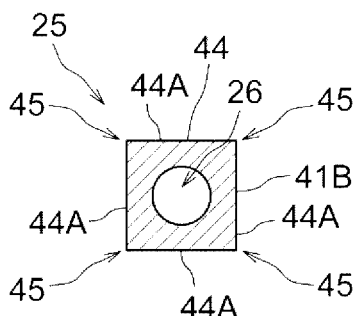

[Fig. 23]
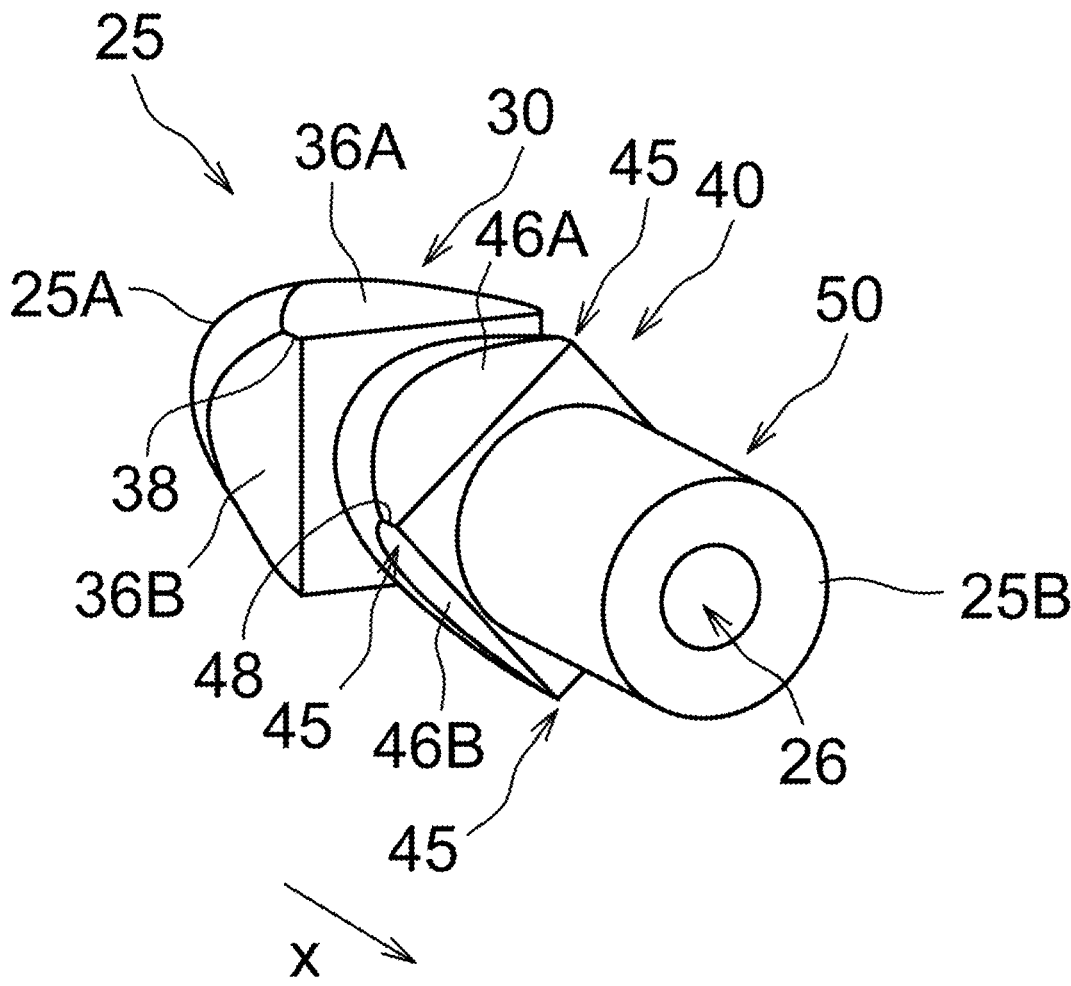

RADIO FREQUENCY SURGICAL INSTRUMENT

TECHNICAL FIELD

The present invention relates to a radio frequency surgical instrument configured to be introduced into a living body via an endoscope.

BACKGROUND ART

Endoscopic surgery such as endoscopic sphincterotomy (EST) needs a surgical instrument used for treatment in a body cavity via an endoscopic surgical instrument insertion channel extending from a nearby position to a tip position. Examples of such a surgical instrument include a papillotomy knife.

A surgical instrument disclosed in Patent Documents 1 and 2 includes a tubular body called a sheath or a tube extending from a tip end to a nearby position, and a conductive wire inserted through the tubular body and partially exposed from the tip end of the surgical instrument. When radio frequency current flows in the wire, a tissue such as a lesion can be incised with use of the exposed portion of the wire. The wire has a tip end portion to which a fixed member or a fixture called a knife chip is fixed, and the tip end portion of the wire is fixed to the tubular body when the fixture is disposed in a lumen of the tubular body.

RELATED ART DOCUMENTS

Patent Documents

Patent Document 1: JP-A-H05-7597
Patent Document 2: JP-A-2000-262537

SUMMARY OF THE INVENTION

Problems to be Solved by the Invention

However, the tubular body may be made of a material having high slidability such as fluororesin, in which case the fixture may not be intimately fixed to the tubular body. When the wire is moved forward or backward with use of an operating handle at the nearby position and the fixture slides relatively to the tubular body, the wire may thus idle or exit the tubular body. Furthermore, the fixture is disposed in a quite thin lumen of the tubular body, and it is thus difficult to bond with use of an adhesive or partially weld the tubular body. In view of the above, it is an object of the present invention to provide a radio frequency surgical instrument enabling a fixture to be intimately fixed to a tubular body such that a wire moved forward or backward with use of an operating handle at a nearby position is prevented from exiting the tubular body or idling.

Solutions to the Problems

According to an embodiment of the present invention that solves the problems described above, a radio frequency surgical instrument includes: a tubular body having a distal end and a proximal end, and provided therein with at least a first lumen and a second lumen; a metal wire having a tip end and a base end, and including a first portion exposed from and disposed outside a distal portion of the tubular body and a second portion disposed in the first lumen; and a fixture fixed to a tip end portion of the wire, being in contact with an inner wall of the first lumen, and having a tip end and a base end; in which the fixture has a first segment at least including a portion decreased in outer diameter toward the tip end and not including a portion increased in outer diameter toward the tip end, and when the first segment is equally tripartitioned into a tip portion, a center portion, and a base portion, a base end of the tip portion in the first segment and a base end of the base portion in the first segment are different in radial sectional shape of the fixture. Such setting of the radial sectional shape in the first segment of the fixture causes appropriate frictional resistance when the fixture is in contact with the inner wall of the first lumen of the tubular body. The fixture can thus be firmly fixed to the tubular body such that the fixture does not slide in the first lumen of the tubular body. Even when the wire is moved forward or backward at a nearby position, the wire can accordingly be prevented from idling or exiting the tubular body.

In the radio frequency surgical instrument, it is preferable that the radial sectional shape of the fixture at the base end of the base portion in the first segment has a contour including a straight line portion.

In the radio frequency surgical instrument, it is preferable that the radial sectional shape of the fixture at the base end of the base portion in the first segment has a contour including two straight line portions crossing each other.

In the radio frequency surgical instrument, it is preferable that the base portion in the first segment of the fixture has an outer surface having a first planar portion and a second planar portion crossing each other, and the first and second planar portions each have a normal line direction different from a direction from the tip end to the base end of the fixture.

In the radio frequency surgical instrument, it is preferable that the radial sectional shape of the fixture at the base end of the tip portion in the first segment has a contour including only a curved line portion.

In the radio frequency surgical instrument, it is preferable that the radial sectional shape of the fixture at a tip end of the base portion in the first segment has an outer diameter larger than a maximum diameter of the first lumen.

In the radio frequency surgical instrument, it is preferable that the radial sectional shape of the fixture at the base end of the tip portion in the first segment is a circle or an oblong, and the radial sectional shape of the fixture at the base end of the base portion in the first segment is a polygon.

In the radio frequency surgical instrument, it is preferable that the first segment consists of a portion positioned close to a base end and having a constant outer diameter, and a portion positioned close to a tip end and having an outer diameter decreased toward the tip end.

In the radio frequency surgical instrument, it is preferable that the fixture further has a second segment positioned closer to the base end of the fixture than the first segment, the second segment at least including a portion decreased in outer diameter toward the tip end, and not including a portion increased in outer diameter toward the tip end, and the second segment of the fixture has a tip end smaller in outer diameter than the base end of the first segment.

In the radio frequency surgical instrument, it is preferable that when the second segment is equally tripartitioned into a tip portion, a center portion, and a base portion, the radial sectional shape of the fixture at a tip end of the base portion in the second segment has an outer diameter larger than the maximum diameter of the first lumen.

In the radio frequency surgical instrument, it is preferable that when the second segment is equally tripartitioned into a tip portion, a center portion, and a base portion, a base end of the tip portion in the second segment and a base end of the base portion in the second segment are different in radial sectional shape of the fixture.

In the radio frequency surgical instrument, it is preferable that wherein the radial sectional shape of the fixture at the base end of the base portion in the second segment has a circumcircle radially equal to or more than a circumcircle of the radial sectional shape of the fixture at the base end of the base portion in the first segment.

In the radio frequency surgical instrument, it is preferable that the radial sectional shape of the fixture at the base end of the base portion in the second segment is identical to the radial sectional shape of the fixture at the base end of the base portion in the first segment.

In the radio frequency surgical instrument, it is preferable that the first segment is different in length from the second segment in a direction from the tip end to the base end of the fixture.

In the radio frequency surgical instrument, it is preferable that the fixture has a frustum shape in the second segment.

In the radio frequency surgical instrument, it is preferable that the base portion in the second segment is higher in surface roughness than the tip portion in the second segment, the surface roughness being arithmetic mean roughness Ra of reference lengths of roughness curves in a circumferential direction of a surface of the fixture, and the reference lengths being one fourth of a circumferential length of the fixture at respective measurement positions.

Effects of the Invention

In the radio frequency surgical instrument, appropriate frictional resistance is generated when the fixture is in contact with the inner wall of the first lumen of the tubular body. The fixture can thus be firmly fixed to the tubular body such that the fixture does not slide in the first lumen of the tubular body. Even when the wire is moved forward or backward at a nearby position, the wire can accordingly be prevented from idling or exiting the tubular body.

BRIEF DESCRIPTION OF THE DRAWINGS

FIG. 1 is a side view of a radio frequency surgical instrument according to an embodiment of the present invention.

FIG. 2 is an enlarged perspective view of a distal end portion of the radio frequency surgical instrument depicted in FIG. 1.

FIG. 3 is an enlarged sectional view (partially a side view) of the distal end portion of the radio frequency surgical instrument depicted in FIG. 1.

FIG. 4 is a sectional view taken along line IV-IV of the radio frequency surgical instrument depicted in FIG. 3.

FIG. 5 is a sectional view taken along line V-V of the radio frequency surgical instrument depicted in FIG. 3.

FIG. 6 is a perspective view from a tip end, of a fixture depicted in FIG. 1.

FIG. 7 is a perspective view from a base end, of the fixture depicted in FIG. 1. FIG. 8 is a side view depicting a connected state between a fixture depicted in FIG. 3 and a wire.

FIG. 9 is a sectional view at a base end of a base portion in a first segment of the fixture depicted in FIG. 8.

FIG. 10 is a sectional view at a tip end of the base portion in the first segment of the fixture depicted in FIG. 8.

FIG. 11 is a sectional view at a base end of a tip portion in the first segment of the fixture depicted in FIG. 8.

FIG. 12 is a sectional view (partially a side view) depicting a state where the fixture is inserted to a tubular body.

FIG. 13 is a sectional view at a base end of a base portion in a second segment of the fixture depicted in FIG. 8.

FIG. 14 is a sectional view at a tip end of the base portion in the second segment of the fixture depicted in FIG. 8.

FIG. 15 is a sectional view at a base end of a tip portion in the second segment of the fixture depicted in FIG. 8.

FIG. 16 is a side view according to a modification example of the fixture depicted in FIG. 8.

FIG. 17 is a side view according to another modification example of the fixture depicted in FIG. 8.

FIG. 18 is a perspective view according to a modification example of the fixture depicted in FIG. 6.

FIG. 19 is a side view of the fixture depicted in FIG. 18.

FIG. 20 is a sectional view at a base end of a base portion in a second segment of the fixture depicted in FIG. 18.

FIG. 21 is a sectional view at a tip end of the base portion in the second segment of the fixture depicted in FIG. 18.

FIG. 22 is a sectional view at a base end of a tip portion in the second segment of the fixture depicted in FIG. 18.

FIG. 23 is a perspective view, from a base end, according to a modification example of the fixture depicted in FIG. 7.

MODE FOR CARRYING OUT THE INVENTION

Hereinafter, more specific description will now be made to the following embodiment of the present invention. The present invention should not be restricted by the following embodiment but can obviously be implemented with appropriate modifications within a range applicable to purport of the above and below description. Such modifications will be all included in the technical scope of the present invention. Some of the drawings may not include hatching, reference signs of members, or the like for convenience, in which case the specification or any other appropriate drawing should be referred to. Various members in the drawings may not be depicted in actual sizes, because contribution to comprehension of the features of the present invention is prioritized in the drawings.

Description is made to a radio frequency surgical instrument in terms of its configuration with reference to FIGS. 1 to 12. FIG. 1 is a side view of a radio frequency surgical instrument according to an embodiment of the present invention, and FIGS. 2 and 3 are an enlarged perspective view and an enlarged sectional view (partially a side view), respectively, of a distal end portion of the radio frequency surgical instrument depicted in FIG. 1. FIGS. 4 and 5 are a sectional view taken along line IV-IV and a sectional view taken along line V-V, respectively, of the radio frequency surgical instrument depicted in FIG. 3. FIG. 6 is a perspective view from a tip end, of a fixture depicted in FIG. 1, and a FIG. 7 is a perspective view from a base end, of the fixture depicted in FIG. 1. FIG. 8 is a side view depicting a connected state between the fixture depicted in FIG. 3 and a wire. FIGS. 9 to 11 are sectional views at a base end of a base portion, a tip end of the base portion, and a base end of a tip portion, respectively, in a first segment of the fixture depicted in FIG. 8. FIG. 12 is a sectional view (partially a side view) depicting a state where the fixture is inserted to a tubular body. FIG. 4 does not depict a wire 20. A radio frequency surgical instrument 1 includes a tubular body 10, the wire 20, and a fixture 25.

The radio frequency surgical instrument 1 is introduced into a body cavity via an endoscopic surgical instrument insertion channel and is used for an operative method such as EST. Hereinafter, the radio frequency surgical instrument may sometimes be simply called a surgical instrument. The surgical instrument 1 includes an inserted portion 5 to be inserted to an endoscopic surgical instrument insertion channel, and an operating handle 65 connected to a proximal end portion of the inserted portion 5. The inserted portion 5 has a distal end portion preferably provided with a curved portion 8 curved along a shape of the body cavity, for higher workability in the body cavity.

The tubular body 10 according to the present disclosure has a distal portion as a treatment target portion located at a tip side in a longitudinal direction of the tubular body 10 (in other words, a longitudinal axis direction of the tubular body 10). The tubular body 10 has a proximal portion located at a base side in the longitudinal direction of the tubular body 10 and at a nearby position of a user (operator). The wire 20 has a tip end as a first end in a longitudinal axis direction of the wire 20, the first end being distant from the nearby position of the user. The wire 20 has a base end as a second end in the longitudinal axis direction of the wire 20, the second end being opposite to the tip end and close to the nearby position of the user. Unless otherwise specified in the present disclosure, the tubular body 10, the wire 20, or the fixture 25 has an inner portion and an outer portion indicating an inner portion and an outer portion in a radial direction of the tubular body 10, and the inner portion in the radial direction of the tubular body 10, the wire 20, or the fixture 25 indicates a portion close to a longitudinal axis center of the tubular body 10.

The tubular body 10 has a distal end and a proximal end, and is provided therein with at least a first lumen 11 and a second lumen 12. The first lumen 11 is provided therein with the wire 20, and has an inner wall 11A in contact with the fixture 25 to be described later. The second lumen 12 can serve as an insertion path for guide wire or a flow path for liquid injected to the body cavity. Examples of the liquid include a physiological saline solution, hyaluronic acid solution, a contrast medium, as well as liquid containing a medicine or cells.

As depicted in FIGS. 4 and 5, the tubular body 10 may further have a third lumen 13. In this case, the second lumen 12 can serve as an insertion path for the guide wire and the third lumen 13 can serve as a liquid flow path. The first lumen 11 may extend from the distal end to the proximal end of the tubular body 10, and has a distal end that may be disposed proximally relative to the distal end of the tubular body 10. The second lumen 12 and the third lumen 13 preferably extend from the distal end to the proximal end of the tubular body 10. This configuration facilitates insertion of the guide wire and liquid injection.

The first lumen 11, the second lumen 12, and the third lumen 13 have inner diameters that may be equal to or different from one another. The inner diameters may exemplarily increase in the order of the first lumen 11 provided therein with the wire 20, the third lumen 13 for a liquid flow, and the second lumen 12 for insertion of the guide wire. The surgical instrument 1 can thus have a minimized outer diameter for higher body passability.

FIGS. 1 to 3 depict a first opening 14 and a second opening 15 provided in an outer circumferential surface of a distal portion (preferably a distal end portion, and more preferably the curved portion 8 provided adjacent to the distal end) of the tubular body 10. The first opening 14 is positioned distally relative to the second opening 15. The first lumen 11 communicates with the outside of the tubular body 10 via the first opening 14 and the second opening 15.

As depicted in FIG. 3, there may be provided a third opening 16 positioned distally relative to the first opening 14 and the second opening 15 at the distal end portion of the tubular body 10 (preferably in a portion including the distal end of the tubular body 10). In this case, the first lumen 11 may communicate with the outside of the tubular body 10 via the third opening 16. The third opening 16 is preferably positioned distally relative to the fixture 25. Though not depicted, the first lumen 11 has a portion distally relative to the first opening 14 and the second opening 15 (preferably a portion including the distal end of the first lumen 11), and the portion may be sealed.

The distal end portion of the tubular body 10 (preferably the portion including the distal end of the tubular body 10) may be provided with a tapered portion 19 decreased in outer diameter toward the distal end. The surgical instrument 1 can thus have higher body passability. FIG. 2 depicts the first opening 14 and the second opening 15 positioned proximally relative to the tapered portion 19, and the third opening 16 positioned in the tapered portion 19. The fixture 25 is positioned proximally relative to the tapered portion 19.

The tubular body 10 can be provided with another opening allowing projection of the guide wire inserted to the lumen of the tubular body 10 or allowing liquid discharge into the body cavity. FIGS. 2 and 3 exemplarily depict a fourth opening 17 provided at the distal end of the tubular body 10, such that the second lumen 12 communicates with the outside of the tubular body 10 via the fourth opening 17. The guide wire can thus project from the fourth opening 17. The distal end portion of the tubular body 10 (preferably the portion including the distal end of the tubular body 10) has an outer circumferential surface that is preferably provided with a fifth opening 18 such that the third lumen 13 communicates with the outside of the tubular body 10 via the fifth opening 18. This configuration allows liquid discharge into the body cavity via the fifth opening 18. The fifth opening 18 may alternatively be positioned in the tapered portion 19.

The tubular body 10 preferably has flexibility. The tubular body 10 can accordingly be deformed along the shape of the body cavity. The tubular body 10 preferably has elasticity so as to be kept in shape. The tubular body 10 can contain a resin or a metal. Examples of the resin contained in the tubular body 10 include a polyamide resin, a polyester resin, a polyurethane resin, a polyolefin resin, a fluororesin, a vinyl chloride resin, a silicone resin, and natural rubber. The tubular body 10 may contain only one of these resins, or two or more of these resins. Examples of the metal contained in the tubular body 10 include stainless steel such as SUS304 or SUS316, platinum, nickel, cobalt, chromium, titanium, tungsten, gold, Ni—Ti alloy, Co—Cr alloy, or a combination of any of these. Examples of the tubular body 10 include a long metal body having a surface covered with a resin. In particular, the tubular body 10 is preferably a resin tube, and is more preferably a fluororesin tube. The tubular body 10 can have a stacked structure of different materials or an identical material, or a structure including a plurality of tubes joined to each other.

The tubular body 10 is not particularly restricted in terms of its outer shape at a section perpendicular to the longitudinal axis direction of the tubular body 10, and can have a circular shape, an oblong shape, a polygonal shape, a shape obtained by combining any of these shapes, or the like. Examples of the oblong shape include an elliptical shape, an oval shape, and a rectangular shape having rounded corners. The same applies to the following description.

The inner wall 11A of the first lumen 11 has a portion in contact with the fixture 25, and the portion may be uneven. This leads to higher frictional resistance between the tubular body 10 and the fixture 25. In contrast, the second lumen 12 and the third lumen 13 each have an inner wall that preferably has higher slidability than the uneven portion in the inner wall 11A of the first lumen 11. This configuration achieves higher sliding of the guide wire inserted through the second lumen 12, or lower pressure loss of the liquid flowing in the third lumen 13.

The wire 20 includes a portion functioning as a knife portion of a so-called radio frequency knife. The wire 20 is made of a metal and has conductivity. The wire 20 has the tip end and the base end, and has a first portion exposed from and disposed outside the distal portion of the tubular body 10, and a second portion disposed in the first lumen 11. FIG. 3 depicts the wire 20 having the distal portion partially exposed from and disposed outside the tubular body 10 via the first opening 14 and the second opening 15 of the tubular body 10. The wire 20 is disposed in the first lumen 11 at a position proximally relative to the second opening 15 and a position distally relative to the first opening 14. The wire 20 having conductivity can be used as the knife portion of the radio frequency knife when radio frequency current flows in the wire 20. The wire 20 preferably includes a portion disposed in the tubular body 10 and having a surface provided with an insulating layer, and a portion exposed from and disposed outside the tubular body 10 and provided with no insulating layer. This configuration enables only the portion not provided with any insulating layer of the wire 20 to be used as the knife portion. In the wire 20, the portion exposed from and disposed outside the tubular body 10 is shorter than the portion disposed in the first lumen 11 of the tubular body 10.

The wire 20 entirely extends from the distal end portion to the proximal end portion of the tubular body 10. In FIG. 3, the wire 20 has a tip end portion to which the fixture 25 is fixed, and the fixture 25 is in contact with the inner wall 11A of the first lumen 11 of the tubular body 10. Though not depicted, the wire 20 may have a portion in contact with the inner wall 11A of the first lumen 11 of the tubular body 10.

The wire 20 has a base end portion connected to operating handle 65 to be described later. The base end portion of the wire 20 is connected to a radio frequency power source so as to securely have electric continuity. When the wire 20 is moved forward or backward with use of the operating handle 65, the portion of the wire 20 exposed from and disposed outside the tubular body 10 can be changed in length and bending degree. The knife can thus be changed in shape in accordance with a manual technique. The operating handle 65 can also be used to change a curved degree of the distal portion and the curved portion 8 of the tubular body 10.

The wire 20 is preferably made of an elastically deformable material. The wire 20 has elasticity so as to be changed in shape along the tubular body 10. The wire 20 can be exemplarily made of a superelastic alloy such as an Ni—Ti alloy, or stainless steel such as SUS303, SUS304, or SUS316. The wire 20 may be constituted by a single member, or a plurality of members joined halfway in the longitudinal axis direction. The wire 20 can be joined by caulking ends of a plurality of wires 20 with a metal tube, welding, bonding, or the like. The wire 20 may include a single wire or a twisted wire obtained from single wires. The wire 20 including the single wire leads to facilitated manufacture. The wire 20 including the twisted wire achieves improved strength, for easier transfer of operation at the nearby position to a distal end portion of the surgical instrument 1.

The fixture 25 is provided to fix the wire 20 to the tubular body 10. As depicted in FIG. 3, the fixture 25 is fixed to the tip end portion of the wire 20, and is in contact with the inner wall 11A of the first lumen 11. As depicted in FIGS. 6 to 8, the fixture 25 has a tip end 25A and a base end 25B. The fixture 25 in contact with the inner wall 11A of the first lumen 11 generates frictional resistance so as to fix the fixture 25 to the tubular body 10. As depicted in FIGS. 3 and 8, the tip end 25A of the fixture 25 is positioned close to the tip end of the wire 20, and a direction x from the tip end 25A to the base end 25B of the fixture 25 matches a direction from the tip end to the base end of the wire 20.

As depicted in FIG. 3, the fixture 25 can be disposed in the first lumen 11 such that the tip end 25A of the fixture 25 is directed toward the distal end of the tubular body 10. The longitudinal axis direction of the wire 20 thus substantially extends from the distal end portion to the proximal end portion of the tubular body 10 to prevent kinking of the wire 20. The surgical instrument 1 thus configured can be obtained by disposing the fixture 25 distally relative to the first opening 14.

Though not depicted, the fixture 25 may be disposed in the first lumen 11 such that the tip end 25A of the fixture 25 is directed toward the proximal end of the tubular body 10. In this case, a portion in the longitudinal axis direction of the wire 20 is folded back. The portion of the wire 20 exposed from and disposed outside the tubular body 10 can thus extend to project radially outward from the tubular body 10. The surgical instrument 1 thus configured can be obtained by disposing the fixture 25 between the first opening 14 and the second opening 15.

As depicted in FIGS. 6 to 12, the fixture 25 at least has a first segment 30 including a portion having an outer diameter decreased toward the tip end 25A and not including a portion having an outer diameter increased toward the tip end 25A. When the first segment 30 is equally tripartitioned into a tip portion 31, a center portion 32, and a base portion 33, a base end 31B of the tip portion 31 in the first segment 30 and a base end 33B of the base portion 33 in the first segment 30 are different in radial sectional shape of the fixture 25. Such setting of the radial sectional shape in the first segment 30 of the fixture 25 causes appropriate frictional resistance when the fixture 25 is in contact with the inner wall 11A of the first lumen 11 of the tubular body 10. The fixture 25 can thus be firmly fixed to the tubular body 10 such that the fixture 25 does not slide in the first lumen 11 of the tubular body 10. Even when the wire 20 is moved forward or backward at the nearby position, the wire 20 can accordingly be prevented from idling or exiting the tubular body 10. Adoption of the fixture 25 allows the fixture 25 to be disposed in a quite thin lumen of the tubular body 10. Even if it is difficult to bond with use of an adhesive or partially weld the tubular body 10 or even if the tubular body 10 is made of a material such as a fluororesin that is difficult to be fixed by bonding, the fixture 25 can be fixed so as not to slide in the first lumen 11 of the tubular body 10.

The first segment 30 is constituted only by (a) the portion having the outer diameter decreased toward the tip end 25A, or (b) a portion having a constant and unchanged outer diameter and the portion having the outer diameter decreased toward the tip end 25A. That is, the first segment 30 does not include any portion having the outer diameter of the fixture 25 increased toward the tip end 25A.

As depicted in FIG. 8, the first segment 30 preferably consists of a portion positioned close to the base end 25B and having a constant outer diameter, and a portion positioned close to the tip end 25A and having an outer diameter decreased toward the tip end 25A. Specifically, in FIG. 8, the outer diameter of the fixture 25 is constant and unchanged at the base end of the base portion 33, and is decreased toward the tip end 25A in a portion distally relative to a substantially center position in the base portion 33. The first segment 30 has the portion having the constant outer diameter at the base end 25B, so that the fixture 25 is firmly fixed in the first lumen 11 of the tubular body 10.

The portion having the constant and unchanged outer diameter in the first segment 30 of the fixture 25 can have a prism shape, a columnar shape, an elliptic cylinder shape, or the like. The portion decreased in outer diameter toward the tip end in the first segment 30 of the fixture 25 can exemplarily have a frustum shape such as a truncated pyramid shape, a truncated cone shape, an eliptic truncated cone shape, or a truncated pyramid shape having rounded corners.

The radial sectional shape (outer shape) in the first segment 30 of the fixture 25 can be a circle, an oblong, a polygon, or a shape obtained by combining any of these shapes.

The first segment 30 has been disposed partially at the fixture 25. In particular, the first segment 30 is preferably positioned at the most tip end of the fixture 25. The first segment 30 can thus be positioned distant from an insertion port (the first opening 14 in FIG. 3) of the fixture 25 of the tubular body 10, so that the fixture 25 is less likely to exit the tubular body 10.

Though not depicted, the fixture 25 may be constituted only by the first segment 30. That is, the tip end of the first segment 30 may match the tip end 25A of the fixture 25, and the base end of the first segment 30 may match the base end 25B of the fixture 25.

As depicted in FIG. 12, the base end 33B of the base portion 33 in the first segment 30 of the fixture 25 is preferably in contact with the inner wall 11A of the first lumen 11 of the tubular body 10. The base portion 33 in the first segment 30 of the fixture 25 is more preferred to be entirely in contact with the inner wall 11A of the first lumen 11 of the tubular body 10. The fixture 25 can thus be firmly fixed to the tubular body 10.

As depicted in FIG. 12, the radial sectional shape of the fixture 25 at the base end 33B of the base portion 33 in the first segment 30 has an outer diameter that is preferably larger than a maximum diameter of the first lumen 11. The outer diameter of the fixture 25 is set in this manner such that the fixture 25 is easily buried in the inner wall 11A of the tubular body 10. The fixture 25 can accordingly be firmly fixed to the tubular body 10 such that the fixture 25 does not slide in the first lumen 11 of the tubular body 10.

As depicted in FIG. 9, the radial sectional shape of the fixture 25 at the base end 33B of the base portion 33 in the first segment 30 has a contour 34 preferably including a straight line portion 34A. In the radial section of the fixture 25, the fixture 25 is thus easily in contact with the tubular body 10 such that the straight line portion 34A is buried in the inner wall 11A of the first lumen 11 of the tubular body 10.

As depicted in FIG. 9, the radial sectional shape of the fixture 25 at the base end 33B of the base portion 33 in the first segment 30 has the contour 34 preferably including two straight line portions 34A crossing each other. In this case, the two straight line portions 34A crossing each other preferably form a corner 35. The corner 35 is provided such that the fixture 25 is easily in contact with so as to be more deeply buried in the inner wall 11A of the tubular body 10. In FIG. 9, in the radial section of the fixture 25 at the base end 33B of the base portion 33 in the first segment 30, the two straight line portions 34A crossing each other form four corners 35. In the radial section of the fixture 25 at the base end 33B of the base portion 33 in the first segment 30, the corners 35 are preferred to be aligned in a circumferential direction of the fixture 25, and are more preferred to be aligned at equal intervals in the circumferential direction.

The radial sectional shape of the fixture 25 at the base end 33B of the base portion 33 in the first segment 30 is preferably a polygon. In FIG. 9, the radial sectional shape of the fixture 25 at the base end 33B of the base portion 33 in the first segment 30 is a quadrilateral.

Though not depicted, the radial sectional shape of the fixture 25 at the base end 33B of the base portion 33 in the first segment 30 has the contour 34 that may include a curved line portion.

In a predetermined range in the direction x from the tip end 25A to the base end 25B of the fixture 25, the fixture 25 is preferably in contact with the inner wall 11A of the tubular body 10, and is more preferably buried in the inner wall 11A. According to such an aspect, as exemplarily depicted in FIGS. 6 to 8, preferably, the base portion 33 in the first segment 30 of the fixture 25 has an outer surface provided with a first planar portion 36A and a second planar portion 36B crossing each other, and the first and second planar portions 36A and 36B respectively have normal line directions 37A and 37B different from the direction x from the tip end 25A to the base end 25B of the fixture 25. The two planar portions can form an edge 38 that is pointed and extends in the direction x. The edge 38 is buried in the inner wall 11A of the tubular body 10 to firmly fix the fixture 25 to the tubular body 10.

In FIGS. 6 to 8, the first planar portion 36A is in parallel with the direction from the tip end 25A to the base end 25B of the fixture 25. Similarly, the second planar portion 36B is also in parallel with the direction from the tip end 25A to the base end 25B of the fixture 25. The planar portions are thus set in terms of their angles with respect to the direction from the tip end 25A to the base end 25B of the fixture 25, so that the edge 38 can be provided in a wide range in the base portion 33 in the first segment 30.

Though not depicted, the first planar portion 36A may slant to the longitudinal axis direction of the wire 20. For example, the first planar portion 36A may slant to the longitudinal axis direction of the wire 20 by 5 degrees or more, 10 degrees or more, or 15 degrees or more, and may slant by 45 degrees or less, 40 degrees or less, or 35 degrees or less. The same applies to a slant angle of the second planar portion 36B with respect to the longitudinal axis direction of the wire 20. The first planar portion 36A and the second planar portion 36B have slant angles with respect to the longitudinal axis direction of the wire 20, and the slant angles may be equal to or different from each other.

The first planar portion 36A and the second planar portion 36B form an angle that is preferably 150 degrees or less, is more preferably 130 degrees or less, and is further preferably 110 degrees or less. The edge 38 is thus easily buried in the inner wall 11A of the tubular body 10. The angle between the first planar portion 36A and the second planar portion 36B has a lower limit not particularly restricted. The angle can be 20 degrees or more, 40 degrees or more, 60 degrees or more, or the like.

As depicted in FIG. 10, the radial sectional shape of the fixture 25 at a tip end 33A of the base portion 33 in the first segment 30 has the contour 34 preferably including the straight line portion 34A. The fixture 25 is thus easily in contact with so as to be buried in the inner wall 11A of the tubular body 10 also at the tip end 33A of the base portion 33 in the first segment 30 of the fixture 25.

Though not depicted, similarly to the base end 33B of the base portion 33 in the first segment 30, the radial sectional shape of the fixture 25 at the tip end 33A of the base portion 33 has the contour 34 that may include two straight line portions crossing each other. In this case, the two straight line portions 34A crossing each other preferably form a corner. The corner is provided such that the fixture 25 is easily in contact with so as to be more deeply buried in the inner wall 11A of the tubular body 10 also at the tip end 33A of the base portion 33.

As depicted in FIG. 10, the radial sectional shape of the fixture 25 at the tip end 33A of the base portion 33 in the first segment 30 has the contour 34 that may include the straight line portion 34A and a curved line portion 34B. Accordingly, the fixture 25 can be firmly fixed to the tubular body 10 such that the fixture 25 does not slide in the first lumen 11 of the tubular body 10, and the fixture 25 can be easily inserted to the first lumen 11. As depicted in FIG. 10, the radial sectional shape of the fixture 25 at the tip end 33A of the base portion 33 in the first segment 30 has the contour 34 that may include straight line portions 34A and curved line portions 34B disposed alternately. The radial sectional shape of the fixture 25 at the tip end 33A of the base portion 33 in the first segment 30 may thus be a square having rounded corners.

In FIGS. 9 and 10, the tip end 33A of the base portion 33 in the first segment 30 and the base end 33B of the base portion 33 in the first segment 30 are different in radial sectional shape of the fixture 25, however, may be identical to each other.

As depicted in FIG. 12, the tip end 33A of the base portion 33 in the first segment 30 is preferably in contact with the inner wall 11A of the tubular body 10. The fixture 25 is thus likely to be firmly fixed to the tubular body 10. The radial sectional shape of the fixture 25 at the tip end 33A of the base portion 33 in the first segment 30 has an outer diameter more preferably larger than the maximum diameter of the first lumen 11. The fixture 25 is thus easily buried in the tubular body 10 also at the tip end 33A of the base portion 33 in the first segment 30.

As depicted in FIG. 11, the radial sectional shape of the fixture 25 at the base end 31B of the tip portion 31 in the first segment 30 has the contour 34 preferably constituted only by the curved line portion 34B. This inhibits frictional resistance generated between the base end 31B of the tip portion 31 in the first segment 30 of the fixture 25 and the tubular body 10, and the fixture 25 is easily inserted to the first lumen 11. For a similar reason, the radial sectional shape of the fixture 25 at a tip end 31A of the tip portion 31 in the first segment 30 has a contour preferably constituted only by a curved line portion.

Though not depicted, the radial sectional shape of the fixture 25 at the base end 31B of the tip portion 31 in the first segment 30 has the contour 34 that may include a straight line portion. In this case, a total length of straight line portions included in the contour 34 having the radial sectional shape of the fixture 25 at the base end 31B of the tip portion 31 in the first segment 30 is preferably shorter than a total length of straight line portions included in the contour 34 having the radial sectional shape of the fixture 25 at the base end 33B of the base portion 33 in the first segment 30. The straight line portions thus shortened inhibit frictional resistance generated between the base end 31B of the tip portion 31 in the first segment 30 and the tubular body 10, and allow the fixture 25 to be easily inserted to the first lumen 11.

The radial sectional shape of the fixture 25 at the base end 31B of the tip portion 31 in the first segment 30 is preferably a circle or an oblong. In FIG. 11, the radial sectional shape of the fixture 25 at the base end 31B of the tip portion 31 in the first segment 30 is a circle. The fixture 25 can thus be easily inserted to the first lumen 11. For a similar reason, the radial sectional shape of the fixture 25 at the tip end 31A of the tip portion 31 in the first segment 30 is preferably a circle or an oblong.

In FIGS. 10 and 11, the base end 31B of the tip portion 31 in the first segment 30 and the tip end 33A of the base portion 33 in the first segment 30 are different in radial sectional shape of the fixture 25, however, may be identical to each other.

Preferably, the radial sectional shape of the fixture 25 at the base end 31B of the tip portion 31 in the first segment 30 is a circle or an oblong as depicted in FIG. 11, and the radial sectional shape of the fixture 25 at the base end 33B of the base portion 33 in the first segment 30 is a polygon as depicted in FIG. 9. The fixture 25 can thus be firmly fixed to the tubular body 10 at the base portion 33 side in the first segment 30 of the fixture 25. Furthermore, the fixture 25 is easily inserted to the first lumen 11 at the tip portion 31 side in the first segment 30 of the fixture 25.

As depicted in FIG. 12, the tip portion 31 in the first segment 30 of the fixture 25 may be in contact with the inner wall 11A of the tubular body 10. This configuration leads to increase in contact area between the fixture 25 and the tubular body 10, for firm fixing of the fixture 25 to the tubular body 10. Though not depicted, the tip portion 31 in the first segment 30 of the fixture 25 may be entirely in contact with the inner wall 11A of the tubular body 10. The radial sectional shape of the fixture 25 at the tip end 31A of the tip portion 31 in the first segment 30 has an outer diameter that may be larger than the maximum diameter of the first lumen 11.

In order to secure easy insertion of the fixture 25 to the first lumen 11, at least part of the tip portion 31 in the first segment 30 of the fixture 25 may not be in contact with the inner wall 11A of the tubular body 10. For example, the tip end 31A of the tip portion 31 in the first segment 30 of the fixture 25 may not be in contact with the inner wall 11A of the tubular body 10.

The base portion 33 in the first segment 30 is preferably higher in surface roughness than the tip portion 31 in the first segment 30. The base portion 33 in the first segment 30 of the fixture 25 in contact with the inner wall 11A of the first lumen 11 of the tubular body 10 can thus generate appropriate frictional resistance. Furthermore, the tip portion 31 in the first segment 30 is easily inserted to the first lumen 11. The surface roughness is arithmetic mean roughness Ra of reference lengths of roughness curves in a circumferential direction of a surface of the fixture 25, and the reference lengths are one fourth of a circumferential length of the fixture 25 at respective measurement positions.

The arithmetic mean roughness Ra corresponds to arithmetic mean roughness Ra prescribed by JIS B 0601 (2001), and is measured in accordance with JIS B 0633 (2001). The arithmetic mean roughness Ra is measured with use of a measuring machine (e.g. ultra-precision point autofocus probe 3D measuring instrument manufactured by Mitaka Kohki Co., Ltd., model: NH-3SP) prescribed by JIS B 0651 (2001).

The fixture 25 may include a plurality of first segments 30. The plurality of first segments 30 can be aligned in the direction x from the tip end 25A to the base end 25B of the fixture 25. Provision of the plurality of first segments 30 leads to increase in contact area between the fixture 25 and the tubular body 10, for firmer fixing of the fixture 25 to the tubular body 10. The tip end of the first segment 30 disposed closest to the tip end is preferably disposed in a portion including the tip end 25A of the fixture 25.

Preferably, the fixture 25 further has a second segment 40 positioned closer to the base end 25B of the fixture 25 than the first segment 30, the second segment at least including a portion decreased in outer diameter toward the tip end 25A, and not including a portion increased in outer diameter toward the tip end 25A, and the second segment 40 of the fixture 25 has a tip end smaller in outer diameter than the base end of the first segment 30. Provision of the second segment 40 leads to increase in contact area between the fixture 25 and the tubular body 10, for firmer fixing of the fixture 25 to the tubular body 10.

The second segment 40 is constituted only by (a) the portion having the outer diameter decreased toward the tip end 25A, or (b) a portion having a constant and unchanged outer diameter and the portion having the outer diameter decreased toward the tip end 25A. That is, similarly to the first segment 30, the second segment 40 does not include any portion having the outer diameter of the fixture 25 increased toward the tip end 25A.

Similarly to the first segment 30, the portion having constant and unchanged outer diameter in the second segment 40 of the fixture 25 can have a prism shape, a columnar shape, an elliptic cylinder shape, or the like. The portion decreased in outer diameter toward the tip end in the second segment 40 of the fixture 25 can exemplarily have a frustum shape such as a truncated pyramid shape, a truncated cone shape, an eliptic truncated cone shape, or a truncated pyramid shape having rounded corners. The second segment 40 of the fixture 25 may be identical to or different from the first segment 30 in term of its shape.

The radial sectional shape (outer shape) in the second segment 40 of the fixture 25 can be a circle, an oblong, a polygon, or a shape obtained by combining any of these shapes.

In FIGS. 6 to 8, the first segment 30 is provided close to the tip end 25A of the fixture 25, and the second segment 40 is provided closer to the base end 25B of the fixture 25 than the first segment 30. The second segment 40 is equally tripartitioned into a tip portion 41, a center portion 42, and a base portion 43. FIGS. 13 to 15 are radial sectional views at a base end 43B of the base portion 43, a tip end 43A of the base portion 43, and a base end 41B of the tip portion 41, respectively, in the second segment 40 of the fixture 25 depicted in FIG. 8. According to an aspect of FIGS. 13 and 15, similarly to the first segment 30, the base end 41B of the tip portion 41 in the second segment 40 and the base end 43B of the base portion 43 in the second segment 40 are different in radial sectional shape of the fixture 25. According to this aspect, the second segment 40 can be regarded as the first segment 30. In other words, the surgical instrument 1 depicted in FIGS. 6 to 8 has two first segments 30.

As depicted in FIGS. 6 to 8, the second segment 40 is preferably adjacent to the first segment 30. This disposition restricts a portion increased in rigidity of the tubular body 10 by insertion of the fixture 25. Though not depicted, the second segment 40 may alternatively be disposed distant from the first segment 30.

In order to more firmly fix the fixture 25 to the tubular body 10, the second segment 40 is preferred to be also configured as follows for a reason similar to that for the first segment 30.

As depicted in FIG. 12, the base end 43B of the base portion 43 in the second segment 40 of the fixture 25 is preferably in contact with the inner wall 11A of the first lumen 11 of the tubular body 10. The base portion 43 in the second segment 40 of the fixture 25 is more preferred to be entirely in contact with the inner wall 11A of the first lumen 11 of the tubular body 10. Furthermore, the radial sectional shape of the fixture 25 at the base end 43B of the base portion 43 in the second segment 40 has an outer diameter that is preferably larger than the maximum diameter of the first lumen 11.

As depicted in FIG. 13, the radial sectional shape of the fixture 25 at the base end 43B of the base portion 43 in the second segment 40 has a contour 44 preferably including a straight line portion 44A.

As depicted in FIG. 13, the radial sectional shape of the fixture 25 at the base end 43B of the base portion 43 in the second segment 40 has the contour 44 preferably including two straight line portions 44A crossing each other. In this case, the two straight line portions 44A crossing each other preferably form a corner 45 in the radial section of the fixture 25. In the radial section of the fixture 25 at the base end 43B of the base portion 43 in the second segment 40, the corners 45 are preferred to be aligned in the circumferential direction of the fixture 25, and are more preferred to be aligned at equal intervals in the circumferential direction.

The radial sectional shape of the fixture 25 at the base end 43B of the base portion 43 in the second segment 40 is preferably a polygon. In FIG. 13, the radial sectional shape of the fixture 25 at the base end 43B of the base portion 43 in the second segment 40 is a quadrilateral.

As shown in FIG. 23, the corners 35 of the base portion 33 in the first segment 30 and the corners 45 of the base portion 43 in the second segment 40 have tip ends preferably disposed at circumferentially different positions of the fixture 25. The corners 35 and 45 thus displaced from each other achieve firmer fixing of the fixture 25 to the tubular body 10.

Though not depicted, the radial sectional shape of the fixture 25 at the base end 43B of the base portion 43 in the second segment 40 may be rotationally symmetric with respect to the radial sectional shape of the fixture 25 at the base end 33B of the base portion 33 in the first segment 30.

Though not depicted, the radial sectional shape of the fixture 25 at the base end 43B of the base portion 43 in the second segment 40 has the contour 44 that may include a curved line portion.

In a predetermined range in the direction x from the tip end 25A to the base end 25B of the fixture 25, the second segment 40 of the fixture 25 is preferably in contact with the inner wall 11A of the tubular body 10, and is more preferably buried in the inner wall 11A. According to such an aspect, as depicted in FIGS. 6 to 8, the base portion 43 in the second segment 40 of the fixture 25 has an outer surface provided with a first planar portion 46A and a second planar portion 46B crossing each other. In this case, a normal line direction 47A of the first planar portion 46A and a normal line direction 47B of the second planar portion 46B are each preferably different from the direction x from the tip end 25A to the base end 25B of the fixture 25. There can thus be provided an edge 48 as in the first segment 30. Similarly to the corners, the edge 38 of the base portion 33 in the first segment 30 and the edge 48 of the base portion 43 in the second segment 40 are preferably disposed at circumferentially different positions of the fixture 25.

The first planar portion 46A and the second planar portion 46B in the second segment 40 each have an angle to the longitudinal axis direction of the wire 20, and the angle can be set as in the first segment 30. Furthermore, the first planar portion 46A and the second planar portion 46B form an angle that can be set similarly to the angle between the first planar portion 36A and the second planar portion 36B.

As depicted in FIG. 14, the radial sectional shape of the fixture 25 at the tip end 43A of the base portion 43 in the second segment 40 has the contour 44 preferably including the straight line portion 44A. Though not depicted, the radial sectional shape of the fixture 25 at the tip end 43A of the base portion 43 in the second segment 40 has the contour 44 that may include two straight line portions crossing each other. The radial sectional shape of the fixture 25 at the tip end 43A of the base portion 43 in the second segment 40 has the contour 44 that may include the straight line portion 44A and a curved line portion 44B. In FIGS. 13 and 14, the tip end 43A of the base portion 43 in the second segment 40 and the base end 43B of the base portion 43 in the second segment 40 are different in radial sectional shape of the fixture 25, or may be identical to each other.

As depicted in FIG. 12, the tip end 43A of the base portion 43 in the second segment 40 is preferably in contact with the inner wall 11A of the tubular body 10. The radial sectional shape of the fixture 25 at the tip end 43A of the base portion 43 in the second segment 40 has an outer diameter that is preferably larger than the maximum diameter of the first lumen 11. The fixture 25 is thus easily buried in the tubular body 10 also at the tip end 43A of the base portion 43 in the second segment 40.

The radial sectional shape of the fixture 25 at the base end 41B of the tip portion 41 in the second segment 40 may be identical to the radial sectional shape of the fixture 25 at the base end 31B of the tip portion 31 in the first segment 30, or may be different therefrom.

The radial sectional shape of the fixture 25 at the base end 41B of the tip portion 41 in the second segment 40 has the contour 44 that may include a straight line portion, a curved line portion, or both the straight line portion and the curved line portion.

As depicted in FIGS. 14 and 15, the tip end 43A of the base portion 43 in the second segment 40 and the base end 43B of the base portion 43 in the second segment 40 may be different in radial sectional shape of the fixture 25.

As depicted in FIGS. 13 and 15, the base end 41B of the tip portion 41 in the second segment 40 and the base end 43B of the base portion 43 in the second segment 40 may be different in radial sectional shape of the fixture 25. At least the base end 43B of the base portion 43 in the second segment 40 has been shaped to be easily in contact with the inner wall 11A of the tubular body 10.

As depicted in FIGS. 13 and 15, the base end 41B of the tip portion 41 in the second segment 40 and the tip end 43A of the base portion 43 in the second segment 40 may be different in radial sectional shape of the fixture 25.

As depicted in FIGS. 9 and 13, the radial sectional shape of the fixture 25 at the base end 43B of the base portion 43 in the second segment 40 has a circumcircle 49 that is preferred to be radially equal to or more than a circumcircle 39 of the radial sectional shape of the fixture 25 at the base end 33B of the base portion 33 in the first segment 30. The second segment 40 is thus more easily in contact with the inner wall 11A of the tubular body 10 than the first segment 30, so that the fixture 25 is likely to be fixed more firmly to the tubular body 10.

As depicted in FIGS. 9 and 13, the radial sectional shape of the fixture 25 at the base end 43B of the base portion 43 in the second segment 40 is preferably identical to the radial sectional shape of the fixture 25 at the base end 33B of the base portion 33 in the first segment 30. The fixture 25 is thus set in terms of its shape in the first segment 30 and in the second segment 40, for easier manufacture of the fixture 25.

The tip portion of the first segment 30 of the fixture 25 is preferably provided with a function of securing easy insertion of the fixture 25 to the tubular body 10, and the base portion of the first segment 30 is preferably provided with a function of firmly fixing the fixture 25 to the tubular body 10. The second segment 40 is provided with the function of firmly fixing the fixture 25 to the tubular body 10. In order to enjoy both effects of easy insertion of the fixture 25 to the tubular body 10 and firm fixing of the fixture 25 to the tubular body 10, the first segment 30 and the second segment 40 can be differentiated in length in the direction x from the tip end 25A to the base end 25B of the fixture 25.

FIGS. 16 and 17 are side views according to modification examples of the fixture depicted in FIG. 8. As depicted in FIG. 16, the first segment 30 is preferably longer than the second segment 40 in the direction x from the tip end 25A to the base end 25B of the fixture 25. This configuration secures easy insertion of the fixture 25 to the tubular body 10.

As depicted in FIG. 17, the first segment 30 is preferably shorter than the second segment 40 in the direction x from the tip end 25A to the base end 25B of the fixture 25. The fixture 25 is thus likely to be firmly fixed to the tubular body 10.

The base portion 43 in the second segment 40 is preferably higher in surface roughness than the tip portion 41 in the second segment 40. The base portion 43 in the second segment 40 of the fixture 25 in contact with the inner wall 11A of the first lumen 11 of the tubular body 10 can thus generate appropriate frictional resistance. The surface roughness of the second segment 40 can be measured in a manner similar to measurement of the first segment 30.

FIGS. 18 and 19 are a perspective view and a side view, respectively, according to a modification example of the fixture 25 depicted in FIG. 6. FIGS. 20 to 22 are radial sectional views at the base end 43B of the base portion 43, the tip end 43A of the base portion 43, and the base end 41B of the tip portion 41, respectively, in the second segment 40 of the fixture 25 depicted in FIG. 19.

As depicted in FIGS. 20 and 21, the contour 44 of the radial sectional shape of the fixture 25 at the base end 43B of the base portion 43 in the second segment 40 and the contour 44 of the radial sectional shape of the fixture 25 at the tip end 43A of the base portion 43 are preferred to each include the corner 45. The fixture 25 is thus easily in contact with so as to be more deeply buried in the inner wall 11A of the tubular body 10 in the second segment 40. Though not depicted, the contour 44 of the radial sectional shape of the fixture 25 in the entire base portion 43 in the second segment 40 preferably includes the corner 45.

As depicted in FIGS. 20 and 21, the base end 43B of the base portion 43 and the tip end 43A of the base portion 43 in the second segment 40 may be identical in radial sectional shape of the fixture 25. Being identical in sectional shape indicates being identical in type of the sectional shape, and also includes being similar in shape.

Though not depicted, the base end 43B of the base portion 43 and the tip end 43A of the base portion 43 in the second segment 40 may be rotationally symmetric with respect to each other in radial sectional shape of the fixture 25. In this case, the corner 45 at the base end 43B of the base portion 43 and the corner 45 at the tip end 43A of the base portion 43 in the second segment 40 have tip ends preferably disposed at circumferentially different positions of the fixture 25. The corners 45 thus differently positioned achieve firmer fixing of the fixture 25 to the tubular body 10.

As depicted in FIG. 22, the radial sectional shape of the fixture 25 at the base end 41B of the tip portion 41 in the second segment 40 is a quadrilateral. According to the aspect of FIG. 22, the base end 41B of the tip portion 41 in the second segment 40 also has the function of fixing the fixture 25 to the tubular body 10.

As depicted in FIGS. 20 and 22, the base end 41B of the tip portion 41 in the second segment 40 and the base end 43B of the base portion 43 in the second segment 40 may be identical in radial sectional shape of the fixture 25. Furthermore, the base end 41B of the tip portion 41 in the second segment 40 and the tip end 43A of the base portion 43 in the second segment 40 may be identical in radial sectional shape of the fixture 25. In this manner, the radial sectional shape of the fixture 25 may be identical at any position in the second segment 40. The identical sectional shape facilitates provision of the second segment 40 of the fixture 20.

Furthermore, the fixture 25 preferably has a third segment 50 positioned closer to the base end 25B side than the first segment 30. The third segment 50 has a maximum outer diameter preferably smaller than the outer diameter at the base end of the first segment 30. Provision of the third segment 50 close to the base end 25B side of the fixture 25 prevents concentration of stress to a joint between the fixture 25 and the wire 20, for inhibition of kinking of the wire 20.

The third segment 50 is preferably disposed adjacent to the first segment 30 or the second segment 40. When the third segment 50 is disposed adjacent to the second segment 40, the second segment 40 and the third segment 50 have a boundary that can be positioned where the fixture 25 is changed stepwise in outer diameter. When the third segment 50 is disposed adjacent to the first segment 30, the first segment 30 and the third segment 50 have a boundary that can be positioned where the fixture 25 is changed stepwise in outer diameter.

As long as kinking of the wire 20 can be inhibited, the maximum outer diameter of the fixture 25 in the third segment 50 may be smaller than the inner diameter of the lumen of the tubular body 10. Meanwhile, the third segment 50 may be at least partially in contact with the inner wall 11A of the first lumen 11. The maximum outer diameter of the fixture 25 in the third segment 50 may be larger than the maximum diameter of the first lumen 11 of the tubular body 10. The third segment 50 of the fixture 25 can thus have the function of fixing to the tubular body 10.

The fixture 25 in the third segment 50 has a radial sectional area that is preferred to be substantially identical in the direction x from the tip end 25A to the base end 25B or be decreased toward the base end 25B. This configuration inhibits kinking of the wire 20 at the base end 25B of the fixture 25.

In the direction x from the tip end 25A to the base end 25B of the fixture 25, the lengths of the first segment 30, the second segment 40, and the third segment 50 are not particularly restricted, and can be equal to or different from one another. The first segment 30 and the second segment 40 mainly contribute to fixing to the tubular body 10, so that at least one of the first segment 30 and the second segment 40 may be longer than the third segment 50.

The fixture 25 can be made of a resin similar to the material for the tubular body 10, or a metal similar to the material for the wire 20. The material for the wire 20 is preferably different in Rockwell hardness from the material for the fixture 25. The material for the wire 20 is more preferably larger in Rockwell hardness than the material for the fixture 25. Such setting in terms of hardness of the wire 20 and the fixture 25 secures elasticity of the wire 20 as well as facilitates surface treatment of the fixture 25. For example, the wire 20 can be made of SUS304 that easily exerts elasticity, and the fixture 25 can be made of SUS303 that is excellent in machinability. The fixture 25 can contain a radiopaque material. This facilitates finding the position of the surgical instrument 1 during X-ray fluoroscopy.

There is no particular restriction in terms of a method of fixing the fixture 25 to the wire 20, but it is possible to adopt caulking, welding, bonding, or the like. In an exemplary case where the fixture 25 has a lumen 26 penetrating from the tip end 25A to the base end 25B, the fixture 25 can be fixed to the tip end portion of the wire 20 by inserting the wire 20 through the lumen 26 and adopting any one of the above fixing methods. FIG. 8 depicts a tip end chip 21 provided at the tip end portion of the wire 20 and having an outer diameter larger than a maximum diameter of the lumen 26 of the fixture 25. The fixture 25 is attached to the wire 20 by inserting the tip end of the wire 20 from a base end of the lumen 26 of the fixture 25 and catching the tip end chip 21 at the tip end 25A of the fixture 25. The tip end chip 21 may be further heated to be welded in order to more firmly fix the fixture 25 to the wire 20. When the fixture 25 and the wire 20 are each made of a metal, the fixture 25 and the wire 20 are preferably fixed by laser welding. Though not depicted, the tip end chip 21 may not be provided at the tip end of the wire 20, the tip end of the wire 20 may be exposed from the tip end 25A of the fixture 25, and the tip end of the wire 20 and the tip end 25A of the fixture 25 may be welded to each other to fix the wire 20 and the fixture 25. The tip end chip 21 can be made of a material similar to the material for the fixture 25.

Description is made to a configuration disposed at the nearby position to move the surgical instrument 1. The operating handle 65 may include a first handle 66 connected to the base end portion of the wire 20 and a second handle 68 connected to the proximal end portion of the tubular body 10. FIG. 1 depicts the first handle 66 provided outside the second handle 68. The first handle 66 is configured to be longitudinally movable relatively to the second handle 68. When the first handle 66 is moved distally or proximally, the portion of the wire 20 exposed from and disposed outside the tubular body 10 can be changed in length and bending degree. The tubular body 10 and the second handle 68 are connected via a separate connection tube 60 and the separate connection tube 60 is provided with a first inlet 61 configured to receive the guide wire. The second handle 68 is provided with a second inlet 67 used to introduce liquid into the second lumen 12 or the third lumen 13 of the tubular body 10. The first handle 66 is provided with a connecting portion 69 with the radio frequency power source. The tubular body 10 and the second handle 68, or the wire 20 and the first handle 66, may be connected directly to each other, or may be connected via a separate member such as the tube 60. These portions can be connected by thermocompression bonding, bonding with use of an adhesive, or the like.

The present application claims benefit of priority based on Japanese Patent application No. 2020-38076 filed on Mar. 5, 2020. The entire contents of the specification of Japanese Patent application No. 2020-38076 filed on Mar. 5, 2020 are incorporated in the present application for reference.

DESCRIPTION OF REFERENCE SIGNS

1 radio frequency surgical instrument
5 inserted portion
8 curved portion
10 tubular body
11 first lumen
11A inner wall of first lumen
12 second lumen
13 third lumen
14 first opening
15 second opening
16 third opening
17 fourth opening
18 fifth opening
20 wire
21 tip end chip
25 fixture
25A tip end of fixture
25B base end of fixture
26 lumen of fixture
30 first segment
31 tip portion
31A tip end of tip portion
31B base end of tip portion
32 center portion
33 base portion
33A tip end of base portion
33B base end of base portion
34 contour
34A straight line portion
34B curved line portion
35 corner
36A first planar portion
36B second planar portion
37A normal line direction
37B normal line direction
38 edge
39 circumcircle
40 second segment
41 tip portion
41A tip end of tip portion
41B base end of tip portion
42 center portion
43 base portion
43A tip end of base portion
43B base end of base portion
44 contour
44A straight line portion
44B curved line portion
45 corner
46A first planar portion
46B second planar portion
47A normal line direction
47B normal line direction
48 edge
49 circumcircle
50 third segment
60 connection tube
61 first inlet
65 operating handle
66 first handle
67 second inlet

68 second handle
69 connecting portion

The invention claimed is:

1. A radio frequency surgical instrument comprising:
a tubular body having a distal end and a proximal end, and provided therein with at least a first lumen and a second lumen;
a metal wire having a tip end and a base end, and including a first portion exposed from and disposed outside a distal portion of the tubular body and a second portion disposed in the first lumen, the metal wire configured such that a radio frequency current is applied thereto; and
a fixture fixed to a tip end portion of the metal wire, being in contact with an inner wall of the first lumen, and having a tip end and a base end, wherein
the fixture has a first segment at least including a portion decreased in outer diameter toward the tip end and not including a portion increased in outer diameter toward the tip end, and
when the first segment is equally tripartitioned into a tip portion, a center portion, and a base portion, a cross-sectional shape of a base end of the tip portion of the first segment is different from a cross-sectional shape of a base end of the base portion of the first segment in a cross-section perpendicular to a longitudinal direction of the fixture, and
the cross-sectional shape of the base end of the base portion of the first segment has a contour including a plurality of corners arranged at equal intervals in a circumferential direction perpendicular to the longitudinal direction, so that the plurality of corners contact with the inner wall of the first lumen of the tubular body.

2. The radio frequency surgical instrument according to claim 1, wherein the contour of the cross-sectional shape of the base end of the base portion of the first segment includes a straight line portion.

3. The radio frequency surgical instrument according to claim 1, wherein the cross-sectional shape of the base end of the base portion of the first segment has a contour including two straight line portions crossing each other.

4. The radio frequency surgical instrument according to claim 1, wherein the base portion of the first segment of the fixture has an outer surface having a first planar portion and a second planar portion crossing each other, and the first and second planar portions each have a normal line direction different from a direction from the tip end to the base end of the fixture.

5. The radio frequency surgical instrument according to claim 1, wherein the cross-sectional shape of the base end of the tip portion of the first segment has a contour including only a curved line portion.

6. The radio frequency surgical instrument according to claim 1, wherein a cross-sectional shape of a tip end of the base portion of the first segment has an outer width larger than a maximum diameter of the first lumen.

7. The radio frequency surgical instrument according to claim 1, wherein the cross-sectional shape of the base end of the tip portion of the first segment is a round shape or an oval shape, and the cross-sectional shape of the base end of the base portion of the first segment is a polygon.

8. The radio frequency surgical instrument according to claim 1, wherein the first segment consists of a portion positioned close to a base end and having a constant outer width, and a portion positioned close to a tip end and having an outer width decreased toward the tip end.

9. The radio frequency surgical instrument according to claim 1, further comprising a connecting portion suitable for connection to a radio frequency power source.

10. The radio frequency surgical instrument according to claim 1, wherein the cross-sectional shape of the base end of the base portion of the first segment is square.

11. The radio frequency surgical instrument according to claim 1, wherein the fixture further has a second segment positioned closer to the base end of the fixture than the first segment, the second segment at least including a portion decreased in outer diameter toward the tip end, and not including a portion increased in outer diameter toward the tip end, and the second segment of the fixture has a tip end smaller in outer diameter than the base end of the first segment.

12. The radio frequency surgical instrument according to claim 11, wherein, when the second segment is equally tripartitioned into a tip portion, a center portion, and a base portion, a cross-sectional shape of a tip end of the base portion of the second segment has an outer diameter larger than a maximum diameter of the first lumen in the cross-section perpendicular to the longitudinal direction of the fixture.

13. The radio frequency surgical instrument according to claim 11, wherein a length of the first segment is different from a length of the second segment in the longitudinal direction of the fixture.

14. The radio frequency surgical instrument according to claim 11, wherein the fixture has a frustum shape in the second segment.

15. The radio frequency surgical instrument according to claim 11, wherein the base portion of the second segment has a higher surface roughness than the tip portion of the second segment, the surface roughness being arithmetic mean roughness Ra of reference lengths of roughness curves of a surface of the fixture in the circumferential direction, and the reference lengths being one fourth of a circumferential length of the fixture at respective measurement positions.

16. The radio frequency surgical instrument according to claim 11, wherein the cross-sectional shape of the base end of the base portion of the second segment has a contour including a plurality of corners, and the first segment and the second segment are arranged so that the plurality of corners of the first segment and the plurality of corners of the second segment are displaced and located at different positions from each other in the circumferential direction of the fixture.

17. The radio frequency surgical instrument according to claim 11, wherein, when the second segment is equally tripartitioned into a tip portion, a center portion, and a base portion, a cross-sectional shape of a base end of the tip portion of the second segment is different from a cross-sectional shape of a base end of the base portion of the second segment in the cross-section perpendicular to the longitudinal direction of the fixture.

18. The radio frequency surgical instrument according to claim 17, wherein the cross-sectional shape of the base end of the base portion of the second segment has a circumference equal to or more than a circumference of a cross-sectional shape of the base end of the base portion of the first segment in the cross-section perpendicular to the longitudinal direction of the fixture.

19. The radio frequency surgical instrument according to claim 17, wherein the cross-sectional shape of the base end of the base portion of the second segment is identical to the cross-sectional shape of the base end of the base portion of the first segment.

\* \* \* \* \*